United States Patent [19]

Kozulic et al.

[11] Patent Number: 5,185,466
[45] Date of Patent: Feb. 9, 1993

[54] HYDROPHILIC AND AMPHIPHATIC MONOMERS, THEIR POLYMERS AND GELS AND HYDROPHOBIC ELECTROPHORESIS

[76] Inventors: Branko Kozulic, Georg Kempfstrasse 7, 8046 Zurich; Urs Heimgartner, Hoschgasse 70, 8008 Zurich, both of Switzerland

[21] Appl. No.: 688,752

[22] Filed: Apr. 22, 1991

Related U.S. Application Data

[63] Continuation-in-part of Ser. No. 293,840, Jan. 5, 1989, abandoned.

[30] Foreign Application Priority Data

Apr. 20, 1990 [GB] United Kingdom ............ 9008873

[51] Int. Cl.$^5$ ............................................ C07C 233/20
[52] U.S. Cl. .................................................. 564/208
[58] Field of Search ........................................ 564/208

[56] References Cited

PUBLICATIONS

Whistler, R. L., Panzer, H. P. and Roberts, H. J.: J. Org. Chem. col. 26, pp. 1583-1588 (1961).

*Primary Examiner*—Joseph L. Schofer
*Assistant Examiner*—Alex H. Walker
*Attorney, Agent, or Firm*—Nikaido, Marmelstein, Murray & Oram

[57] ABSTRACT

An acrylic monomer which is an amino sugar alcohol whose primary or secondary amino group has been derivatized by an acryloyl or a methacryloyl function. The amino group can be linked to any carbon of five or six-carbon sugar alcohols. The acrylic monomer has the formula:

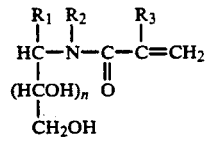

where
$R_1$ is H, $CH_2OH$ or $(CHOH)_mCH_2OH$, m being 1 or 2;
$R_2$ is monohydroxyalkyl, polyhydroxyalkyl or hydrocarbon radical;
$R_3$ is H or $CH_3$; and
n is an integer of 1–4

The acrylic monomer can be polymerized by a free radical polymerization, either alone or with other compounds and materials having polymerizable double bonds. The so formed polymers are linear or branched (cross-linked). The cross-linked polymers are usually in the form of gels. The gels can be polymerized in different forms and shapes, i.e., beads, thin sheets, rods, blocks, etc. and are useful as separation media, e.g., the transparent gels are useful as an anticonvective matrix in electrophoresis, whereas the opaque gels prepared in a bead form are useful in chromatography.

20 Claims, 7 Drawing Sheets

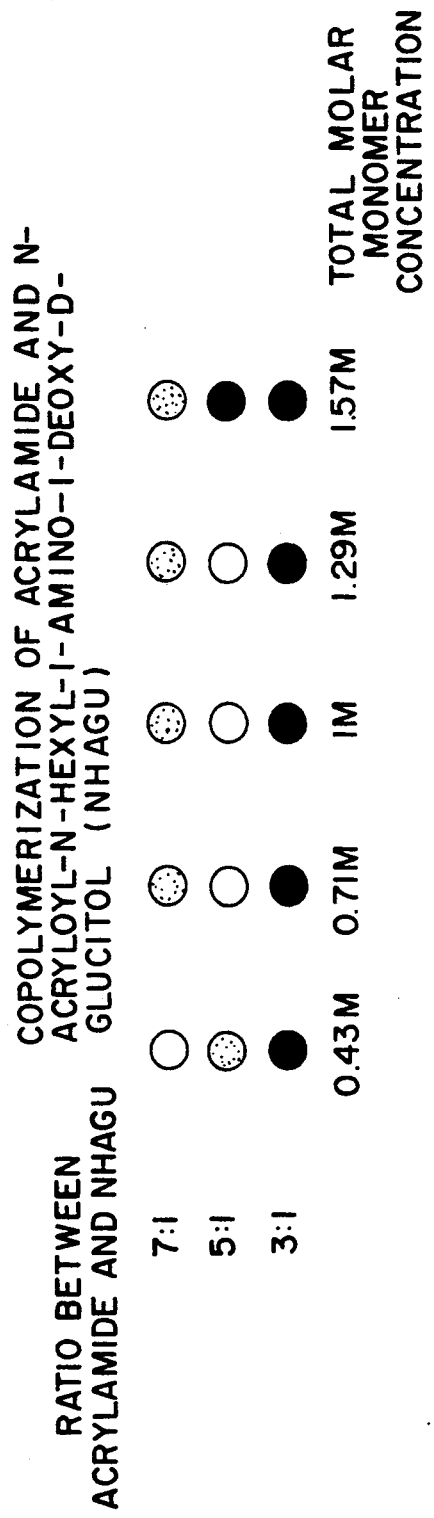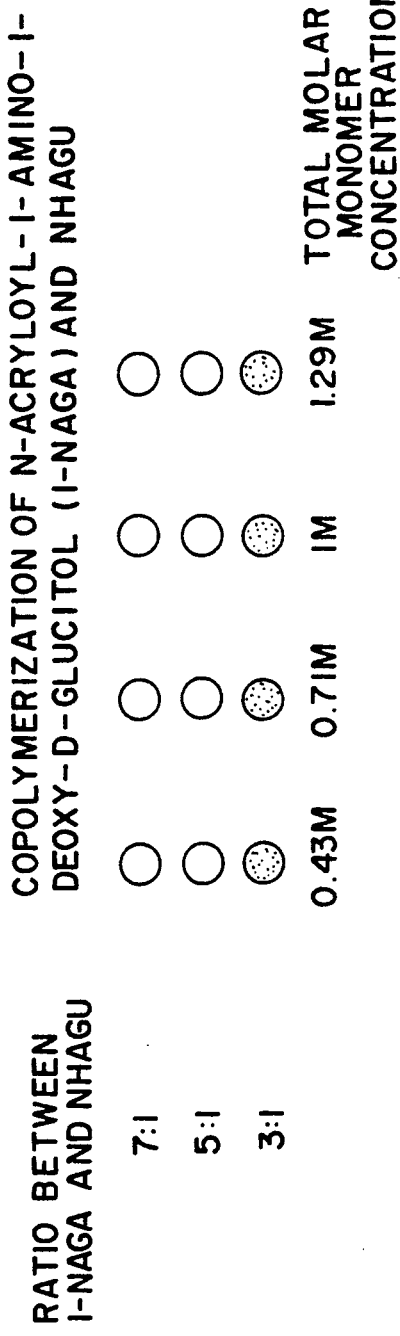

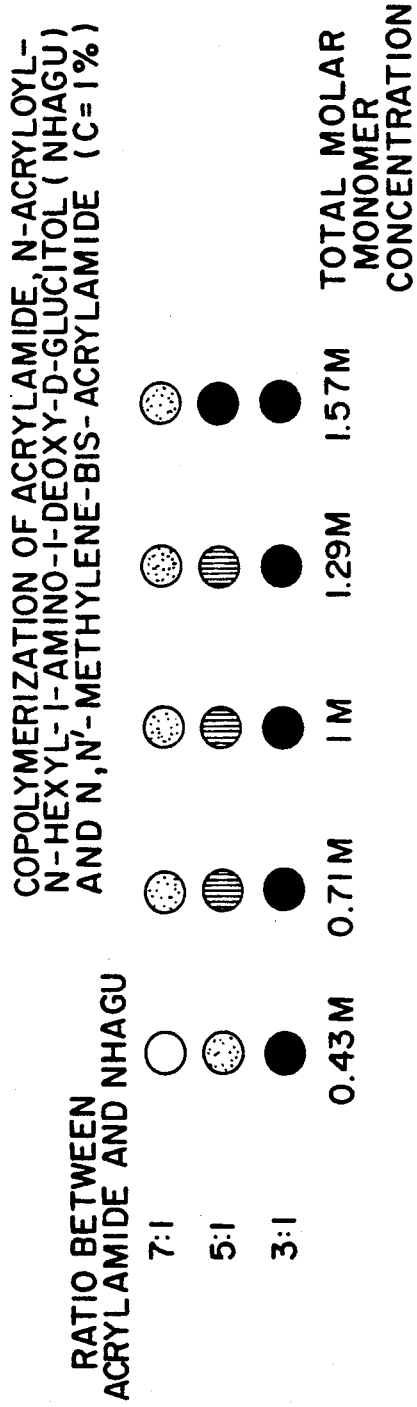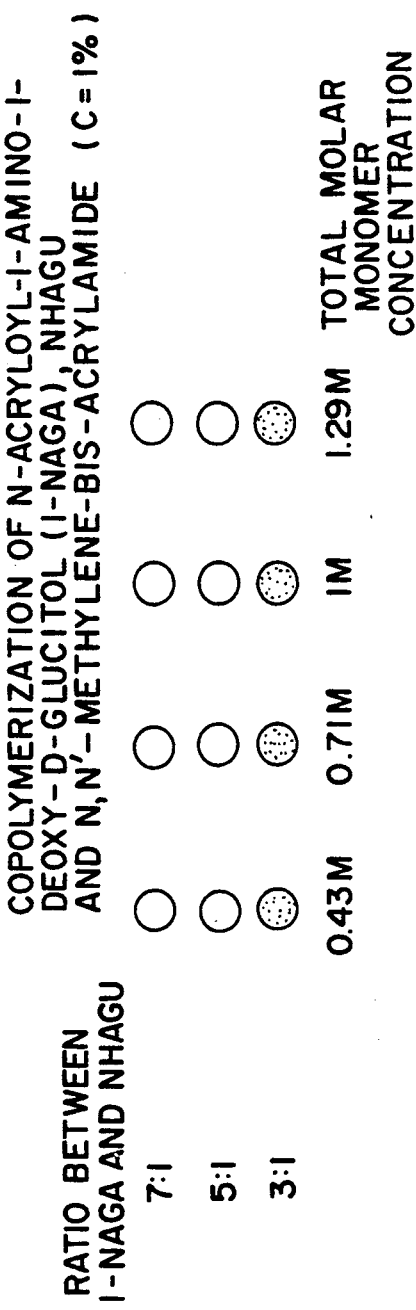

HYDROPHILIC AND AMPHIPHATIC MONOMERS, THEIR POLYMERS AND GELS AND HYDROPHOBIC ELECTROPHORESIS

This application is a continuation-in-part of U.S. application Ser. No. 293,840, filed Jan. 5, 1989, now abandoned.

FIELD OF THE INVENTION

This invention concerns acrylic monomers having a hydrophilic or a hydrophilic and hydrophobic moiety as well as polymers prepared from these monomers. This invention also includes the cross-linked polymers formed from these monomers, as well as these polymers in the form of aqueous gels. These gels are a suitable matrix for electrophoresis. When the gels contain an amphiphatic monomer, electrophoretic migration of some molecules depends on their hydrophobicity.

BACKGROUND OF THE INVENTION

There are two important techniques for separation of biomolecules. Chromatography is generally used for a preparative purification of biological molecules, whereas electrophoresis is the most powerful technique for analysis of the molecules in crude samples and at various stages of a purification procedure.

Each of these two techniques uses separation media of unique properties. Nevertheless, media for both or either chromatography and electrophoresis can be prepared from the same starting material. Until now, only two acrylic monomers have been successfully used to prepare gels for electrophoresis and chromatography. These two monomers are acrylamide and N-acryloyl-tris(hydroxymethyl)-aminomethane (NAT). One of the inventors of the present invention is one of the persons who have introduced the NAT-monomer to prepare poly-NAT gels for electrophoresis (Kozulic, M., Kozulic, B., and Mosbach, K. (1987), R. Anal. Biochem. 21 26 23 2, 2, 506-512 (reference 1); Kozulic, B., Mosbach, K., and Pietrzak., M. (1988), Anal. Biochem. 21 27 20 2, 2, 478-484 (reference 2); and International Patent Application No. PCTEP88/00515) (Reference 3).

The poly-NAT gels possess several advantages over the polyacrylamide gels. In addition to their pronounced hydrophilicity, their most important advantage is the higher porosity of these gels. Since a gel even more hydrophilic and porous than a poly.NAT gel would be beneficial in many applications, a search was made for a monomer which could be polymerized to produce such a gel.

A NAT solution has a molar concentration lower than a polyacrylamide solution of the same weight percentage, because the molecular weight of NAT is about 2.5 fold higher than the molecular weight of acrylamide. The poly-NAT gels have been found to be approximately 3 times more porous than the corresponding polyacrylamide gels, which is in good agreement with the 2.5 fold lower molarity. Thus, one can assume that the lower molar concentration of NAT solutions results, after polymerization, in fewer polymer chains per unit volume, leading to gels of increased porosity. If this assumption is correct, then even more porous gels will be formed from monomers of even higher molecular weight. However, the lack of mechanical strength may be a drawback of gels produced from monomers of very high molecular weight. The optimal properties are expected to be inherent to the monomers of medium size, due to a balanced ratio between the size of the polymer backbone and the size of the side chains present in every repeating unit.

In addition to the size of a monomer, other factors can influence the porosity of a gel. If interactions exist between monomer molecules, or between a monomer and a growing polymer, or between the two growing polymer chains, then as a result of these interactions the polymer chains will not be randomly distributed. They are likely to form some kind of bundles and thus create large pores. It is generally accepted that the high porosity of agarose gels comes from an association of polymer chains during the gelation process. The resulting bundles of polymer chains are presumably held together by hydrogen bonds. Other types of stabilizing forces, such as hydrophobic interaction or ionic bonds, are not compatible with the media that are to be used for electrophoresis or chromatography.

From the above considerations, it appeared that monomers composed of sugar alcohols might form gels with desirable properties. They are hydrophilic, they are of medium size and they have 4-5 hydroxyl groups which could form hydrogen bonds. As shown in the present invention, many such compounds can be conveniently and controllably synthesized. In addition, such synthesized compounds easily polymerize and form gels useful for electrophoresis and chromatography. Two monomers of the general type described herein, N-acryloyl-1-amino-1-deoxy-D-glucitol and N-methacryloyl-1-amino-1-deoxy-D-glucitol, have been synthesized previously (Whistler, R.L., Panzer, H.P., and Roberts, H.J. (1961), J. Org. Chem. Vol. 26 p. 1583-1588), but they were not used to prepare crosslinked gels for electrophoresis or chromatography.

OBJECTIVES OF THE INVENTION

It is an object of the present invention to provide a process (method) for preparation of novel monomers from sugar alcohols.

It is another object of this invention to provide a novel series of polymerizable monomers based on sugar alcohols.

It is another object of the present invention to provide a process (method) for preparation of polymers from these monomers, especially of such polymers that are suitable as media for electrophoresis and chromatography.

It is another object of this invention to provide a novel series of polymers derived from the monomers hereof.

It is a further object of the invention to demonstrate the preparation of gel-systems for separation techniques, e.g., electrophoresis or chromatography, using the polymers of the invention.

Other and additional objects of this invention will become apparent from a consideration of this entire specification as well as the claims appended hereto.

SUMMARY OF THE INVENTION

Fulfilling these objects, one aspect of this invention is directed to monomers composed of amino sugar alcohols having a secondary amino group which has been derived from an acryloyl or a methacryloyl function. The amino group can be linked to any carbon of five or six-carbon sugar alcohols.

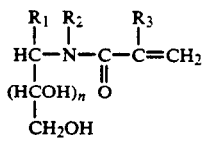

where
$R_1$ is H, $CH_2OH$ or $(CHOH)_m CH_2OH$, m being 1 or 2;

$R_2$ is monohydroxyalkyl, polyhydroxyalkyl or hydrocarbon radical; preferably of about 1-30 carbon atoms;

$R_3$ is H or $CH_3$; and n is an integer of 1-4;

The term monohydroxyalkyl as used here includes aliphatic alcohols having one hydroxy group. The following are non-limiting illustrative of monohydroxyalkyl radical within the scope of this invention: 2-hydroxyethyl, 2-hydroxypropyl, 3-hydroxypropyl, 4hydroxybutyl, 2-hydroxy-2-methyl-propyl, 2-hydroxypentyl, 3- 4-hydroxypentyl, 4-hydroxypentyl, 5-hydroxypentyl, 2methyl-butyl, 3-hydroxy-3-methyl-butyl.

The term polyhydroxyalkyl as used in this invention includes aliphatic alcohols having more than one hydroxy group. The following serve as non-limiting illustrations: 2,3dihydroxypropyl, 2,3-dihydroxybutyl, 2,4-dihydroxybutyl, 3,4dihydroxybutyl, 2,3,4-trihydroxybutyl, 2,3-dihydroxypentyl, 2,4dihydroxypentyl, 2,5-dihydroxypentyl, 3,4-dihydroxypentyl, 3,5dihydroxypentyl, 4,5-dihydroxypentyl, 2,3,4-trihydroxypentyl, 2,4,5-trihydroxypentyl, 2,3,5-trihydroxypentyl, 3,4,5trihydroxypentyl, 2,3,4,5-tetrahydroxypentyl, 2,3-dihydroxyhexyl, 2,4-dihydroxyhexyl, 2,5-dihydroxyhexyl, 2,6-dihydroxyhexyl, 3,4dihydroxyhexyl, 5,6-dihydroxyhexyl, 2,3,4-trihydroxyhexyl, 2,3,5trihydroxyhexyl, 2,3,6-trihydroxyhexyl, 2,4,5-trihydroxyhexyl, 2,4,6-trihydroxyhexyl, 2,5,6-trihydroxyhexyl, 3,4,5trihydroxyhexyl, 3,4,6-trihydroxyhexyl, 3,5,6-trihydroxyhexyl, 4,5,6-trihydroxyhexyl. 2,3,4,5-tetrahydroxyhexyl, 2,4,5,6tetrahydroxyhexyl, 2,3,5,6-tetrahydroxyhexyl, 2,3,4,6tetrahydroxyhexyl, 3,4,5,6-tetrahydroxyhexyl, 2,3,4,5,6pentahydroxyhexyl.

The term hydrocarbon radical as used herein includes aliphatic, cycloalipharic and aromatic (including aliphatic- and cycloaliphatic-substituted aromatic and aromatic-substituted aliphatic and cycloaliphatic) radicals. Where a named radical has several isomeric, including stereoisomeric, forms, all such forms are included. The following are non-limiting illustrative examples of hydrocarbon radicals: ethyl, propyl, butyl, pentyl, hexyl, benzyl, phenylethyl, cyclopentyl, cyclohexyl, methylcyclopentyl, octyl, decyl, dodecyl, octadecyl, naphthyl.

The monomers of the present invention are synthesized by reacting the N-substituted amino group of a sugar alcohol with an activated derivative of acrylic or methacrylic acid, such as acryloyl chloride or methacryloyl chloride. Other activated derivatives, such as acrylic acid anhydride or methacrylic acid anhydride or N-hydroxysuccinimide ester of acrylic or methacrylic acid may be advantageous in some instances. The N-substituted amino sugar alcohols can be prepared in several ways but the most widely used procedure includes reductive amination of the reducing monosaccharide with an amine. Many N-alkyl sugar amino alcohols are known have been used for different applications (references 5-7). Di-alditylamines have also been described (reference 8). The N-substituted alditol amines served as the starting material for the preparation of new monomers disclosed in this invention.

Acylation of the amines with an activated derivative of acrylic or methacrylic acid can be done in different solvents. The choice is determined by the solubility of the amine, the reactivity of the activated derivative of acrylic or methacrylic acid and possible side reactions. For example, alcohols are not suitable solvents if acryloyl or methacryloyl chloride are to be used, due to the predominant reaction between the alcohol solvent and reagent. If the amine is soluble, other solvents, such as for example dioxane or acetonitrile, are suitable. A possible side reaction in such solvents is esterification of one or several hydroxy groups. Water can also be used as solvent. If an acid is liberated during the acylation reaction it is advantageous to neutralize it by a base. It is possible to use inorganic and organic bases and particularly useful are LiOH, NaOH, KOH, $Ca(OH)_2$ and tertiary amines. Alternatively, two moles of the amine can be taken for one mole of the activated acrylic or methacrylic acid derivative and then one mole of the amine serves to neutralize the acid which is liberated.

Water is a preferential solvent for acylation of many alditol amines because they are little soluble in other solvents and because the esterification of the hydroxy groups is less favorable in water. A disadvantage is the potential for hydrolysis of the activated acrylic and methacrylic acid derivatives. By carefully controlling the reaction condition, it is possible to achieve high yields of the alditol acrylamides and methacrylamides. Monomers of the present invention were synthesized substantially by the same procedure.

According to this invention, the acylation reaction is preferentially carried out at a low temperature (0°-15° C.), at a slightly alkaline pH (7.5-11) conditions in a two-phase (preferably water-methylene chloride) system. The amides are separated from the by-products and unreacted starting material preferentially by a combination of an anionic and cationic ion exchanger. The ion exchangers can be used in sequence or as a mixture. The combination of a strong cationic ion exchanger, such as Dowex 50 or Amberlite IR-120, and a weak anion exchanger, such as Amberlite IRA-68, was found particularly suitable. The resulting water solution of pure monomer is poured into crystallization dishes or first partially concentrated by rotary evaporation. It is advantageous to add a small quantity of a polymerization inhibitor (such as for example p-methoxy phenol, phenothiazine, sodiumnitrite, etc.) prior to water evaporation. Some monomers crystallized after the water evaporated, some solidified into a hard mass and some remained as viscous liquids. The solid ones were suitably recrystallized and those which remained in solution were treated with mixed ion exchangers and charcoal prior to polymerization.

The monomers of the present invention can be polymerized by a free radical polymerization using the usual initiators. Examples of such initiators include peroxides, 2,2'-azo-bis-isobutyronitrile and N,N,N',N'-tetramethylethylenediamine plus ammonium or alkali metal persulfate. The polymerization may be a block polymerization or an emulsion polymerization. For block polymerization, the monomer solution containing an initiator is polymerized in a homogenous phase. For emulsion polymerization the monomer solution is dispersed and polymerized in the form of droplets in another phase which is not a good solvent for the monomer.

The monomers may be polymerized either alone or with other compounds and materials having polymerizable double bonds. When monomers of the present invention are polymerized alone or with another monomer having only one double bond, soluble polymers may be formed. Many different monomer combinations were polymerized. The water solubility of the polymers was mainly dependent on four parameters. The hydrophobicity of the amphiphatic monomer substituent, the ratio between hydrophilic and amphiphatic monomers, the type of the hydrophilic monomer and the total monomer concentration.

Examples of water soluble polymers include: a copolymer of acrylamine and N-acryloyl-N-hexyl-1-amino-1-deoxy-D-glucitol, polymerized at 0.43 M total monomer concentration and 7:1 molar ratio of acrylamide to the amphiphatic monomer; and a copolymer composed of N-acryloyl-N-hexyl-1-amino-1-deoxy-D-glucitol and N-acryloyl-1-amino-1-deoxy-D-glucitol polymerized at 0.43 total monomer concentration and 5:1 molar ratio of the hydrophilic to amphiphatic monomer. Some of the monomers when polymerized alone formed water insoluble polymers. Illustrative of these polymers are poly(N-acryloyl-N-butyl-1-amino-1-deoxy-D-galacitol) and poly(N-acryloyl-N-butyl-1-amino-1-deoxy-D-glucitol). The soluble copolymers containing amphiphatic monomers with more hydrophobic residues, especially those with hexyl and octyl groups, behaved as surfactants. When their water solutions were agitated, the foam on the surface remained stable for several hours in many cases. Polymeric surfactants have been previously described (references 9, 10), but they did not comprise amphiphatic monomers.

Cross-linked polymers are formed when the monomers of the present invention were copolymerized with other monomers having at least two double bonds. The cross-linked polymers were usually in the form of gels. The appearance of these gels was transparent or slightly to fully opaque. Transparent, and therefore homogenous, gels were formed when the concentration of the cross-linker was relatively low. In addition, the transparency of gels containing amphiphatic monomers was dependent on the concentration and hydrophobicity of these monomers. Many different combinations were polymerized, as descrited below. Illustrative of transparent gels arepoly(N-acryloyl-N-(2-hydroxyethyl)-1-amino-1-deoxy-D-glucitol-co-N,N'-methylene-bis-acrylamide) containing 6.790 0.210 g of the cross-linker in 100 ml, poly(N-acryloyl-N-ethyl-1-amino-1-deoxy-D-galacitol-co-N,N'-methylene-bis-acryla containing 5.820 g monomer and 0.180 g cross-linker in 100 ml and poly(N-acryloyl-N-hexy-1-amino-1-deoxy-D-glucitol-co-acrylamide-co-N,N'-methylene-bis-acrylamide) containing 1.2 g of the amphiphatic monomer, 2 7 g of acrylamide and 0.04 g of the crosslinker in 100 ml. Unexpectedly, transparent or slightly opaque gels were obtained from some monomers or combinations that had formed insoluble polymers. For example, N-acryloyl-N-butyl-1-amino-1-deoxy-D-galacil.ol when polymerized alone gave a water insoluble polymer, but when polymerized in the presence of a crosslinker it gave an almost transparent gel.

In accord with and fulfilling the objects of this invention, another aspect of this invention is in the use of the polymers of this invention as a gel substrate for separation media of the polymers which have been found to be useful in this utility are those defined above as well as those which are homologous thereto but have only an N-acryloyl or N-methacryloyl single substitution. That is, the polymers which are unusually effective as substrates for use in electro-phoresis or chromatographic separations comprise monomers of repeating unit of:

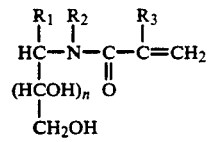

where
$R_1$ is H, $CH_2OH$ or $(CHOH)_m CH_2OH$, m being 1 or 2;

$R_2$ is hydrogen, monohydroxyalkyl, polyhydroxyalkyl or hydrocarbon radical;

$R_3$ is H or $CH_3$; and n is an integer of 1–4

The transparent and slightly opaque gels were useful as a matrix for electrophoresis. Three types of molecules were electrophased in the gels containing the monomers of this invention. The first one is bromphenol blue (3',3'',5',5''-tetrabromophenol sulfonphtalein), a relatively small molecule having three substituted benzene groups and two negative charges (above pH 5). The second type is DNA represented by a series of fragments with sizes from 75 to 23 000 base pairs. Proteins are the third type of molecules electrophased in the new gels.

The electrophoretic migration of bromphenol blue and DNA fragments was compared in several gels, each one being made of a different monomer composition. All gels were polymerized from solutions containing 5.820 g monomer and 0.180 g of N,N'-methylene- C bis-acrylamide in 100 ml. The monomers include N-acryloyl-N-methyl-1-amino-1-deoxy-D-galactitol, N-acryloyl-N-ethyl-1-a deoxy-D-galacitol,N-acryloyl-N-propyl-1-amino-1-deoxy-D-galacitol and N-acryloyl-N-butyl-1-amino-1-deoxy-D-galactitol. Thus the only difference between the monomers was substitution on the amide nitrogen, ranging from methyl to butyl.

Accordingly, the gels differed in their hydrophobicity. The migration rate of bromphenol blue was similar in the gels made of methyl and ethyl monomers. In the first gel the dye migrated slightly behind the 123 base pair (bp) DNA fragment and in the second gel slightly ahead of the 123 bp fragment. More importantly, in the gel with butyl groups bromphenol blue migrated approximately as the 1000 bp fragment.

In addition, at the beginning of electrophoresis, the dye zone was concentrated as it entered the gel and a slight change in color (to pale blue) of brorphenol blue could be observed in this gel. Such effects were not noticed in the other three gels. These findings indicate that electrophoretic migration of bromphenol blue is decreased due to hydrophobic binding to the butyl groups in the gel.

It is important to note that the electrophoretic migration of DNA fragments from 123 to 6000 bp was comparable in all gels, indicating a similar effective porosity of these four gels. The bands were sharper and resolution was better in gels with methyl and propyl than with gels with ethyl and butyl groups. In all gels the 506 and 516 bands (from the 1 kbp standard mixture, BRL) were resolved and at least 10 bands (from the 123 bp standard mixture, BRL) were distinguishable.

The above findings demonstrate that by introducing a new separation principle in gel electrophoresis, that is hydrophobicity, it is possible to resolve molecules otherwise having a similar mobility in a hydrophilic gel. For example, it would be difficult to resolve bromphenol blue and the 123 bp DNA fragment solely on basis of their mobility in the gels composed of monomers containing methyl or ethyl groups. The resolution is, however, very efficient in the gel with butyl groups because due to the hydrophobic interaction in that gel bromphenol blue migrates in this gel in the same manner as a 1000 bp DNA fragment.

Many gels with hydrophobic residues were used for electrophoresis or proteins. The gels were usually composed of acrylamide, amphiphatic monomer and N,N'-methylene-bis-acrylamide. The relative ratios of the three components were chosen to give essentially transparent gels. The composition of gels is conveniently expressed in terms of total monomer concentration (T) in g/100 ml, cross-linker concentration (C) in g of cross-linker/g total monomer $\times 100$ and the molar ratio of the amphiphatic monomer to acrylamide.

When the conversion of monomers to polymers is 100%, the polymer composition will reflect the initial composition of monomers. Although in practice the conversion yield in never 100%, it is convenient to define the gels in terms of their initial monomer compositions.

A typical series of gels was characterized by $T=12$, $C=1$ and the ratio of N-acryloyl-N-hexyl-1-amino-1-deoxy-D-glucitol to acrylamide from 1:20 to 1:160. The gel having no amphiphatic monomer (the blank) contained N-acryloyl-1-amino-1-deoxy-D-glucitol in a molar ratio to acrylamide of 1:20. Bovine serum albumin (BSA) was used as a model protein. When electrophoresed in these gels under standard conditions (reference 11), BSA was not retarded although bromphenol blue was. Actually the protein migrated somewhat longer than the gel with no hexyl groups. Likewise, in gels with octyl groups (molar ratio to acrylamide from 1:40, gel is slightly opaque, to 1:80, transparent gel) no retardation of BSA could be observed.

One common way to make hydrophobic interaction favorable is to increase the salt concentration. This is an accepted practice in hydrophobic chromatography. However, buffers of high ionic strength are not suitable in electrophoresis because they cause excessive heating and reduce the electrophoretic mobility of proteins. Therefore, another way was looked for to increase hydrophobic interactions.

Gel electrophoresis of proteins is sometimes performed in the presence of detergents. Nonionic and zwitterionic detergents are generally used to improve water solubility of hydrophobic proteins, whereas strong anionic cationic detergents are utilized to unfold proteins. Of them, sodium dodecyl sulphate (SDS) is the most widely used. It binds to proteins (1.4 g/g protein) through its hydrocarbon part and rakes them essentially uniformly charged by converting all proteins into a rod-like shape. During gel electrophoresis, larger protein-SDS complexes are more retarded due to the sieving effect of the gel. Since proteins migrate as a function of their side, SDS electrophoresis is often used to estimate the size of an unknown protein.

Detergents are known to decrease or prevent hydrophobic interactions between proteins and hydrophobic molecules in solution, and between [proteins and hydrophobic surfaces. For that purpose they are routinely added into protein solutions that are used in many assays, including immunoassays. Based on prior art, it was therefore reasonable to assume that detergents would also decrease hydrophobic interactions during electrophoresis in a gel containing hydrophobic residues. Nevertheless, the influence of SDS on electrophoretic migration of proteins in the gels with hydrophobic residues was tested. It was surprisingly found that already at 0.02% SDS concentration, the migration of BSA was retarded in the gels having 1:40 and 1:20 molar ratio of N-acryloyl-N-hexyl-1-amino-deoxy-D-glucitol to acrylamide. When the concentration of SDS gas increased to 0.05% the retardation was observed in the gel with 1:160 molar ratio, and the protein migrated only slightly in the 1:20 gel. At 0.1% SDS in the 1:90 gel BSA migrated approximately half the distance it migrated in the control gel. It hardly entered the 1:20 gel. At 0.2% SDS in the 1:160 gel, BSA migrated less than half the distance in the control gel and it remained on top of the 1:40 and 1:20 gels.

The above findings demonstrate that addition of a detergent may be beneficial for hydrophobic interactions between some large molecules and hydrophobic residues in the gel. We propose the following mechanism to account for this finding. Addition of SDS to the gel causes a change in gel structure. The hydrocarbon chain of SDS binds to the hydrocarbon chain of the monomer and makes in negatively charged. The charged complex is better available to the molecules migrating through the gel for two reasons. First, the hydrated sulfate group prevents "hiding" of the hydrocarbon chain in the polymer structura. Second, the electrophoretic force acting on the SDS stretches the whole complex away from the polymer backbone. The incoming protein-SDS complexes have hydrophobic amino acid residues, which may normally have been hidden in the interior of the native molecule, on the surface. When one SDS molecule dissociates (or is electroeluted from the protein amino acid residues, and in its vicinity also one from the matrix, a new complex is formed between the amino acid residues and the hydrophobic group from the matrix. The protein is subsequently either electroeluted or dissociated by SDS from the matrix, but the protein-matrix complex exists long enough to dramatically change the migration rate of a protein.

The increasing retardation effect seen with higher SDS concentrations indicates that the primary role of SDS is to make available the hydrophobic groups from the matrix. Once the protein is hydrophobically bound through multiple points, it may be difficult to release it, as demonstrated by the finding that in the 1:40 and 1:20 gels at 0.2% SDS, the protein remained on the top of the gel.

The above findings clearly show that hydrophobic properties of molecules can be utilized for their electrophoretic resolution. Hydrophobic electrophoresis of some small molecules can be achieved without addition of a detergent. This is probably so because small molecules can penetrate into the gel matrix better and because their hydrophobic residues are more exposed than they are in large molecules. Other molecules may require the presence of the detergent. A charged detergent may be advantageous also for hydrophobic electrophoresis of uncharged molecules. It is known that uncharged molecules can be resolved by capillary electrophoresis in the presence of anionic or cationic detergents (reference 12). The selectivity in hydrophobic electrophoresis introduced herein may be changed by utilizing different concentrations of various detergents. More importantly, the strength of hydrophoblc interactions can be changed by using different hydrophobic residues in the matrix, as demonstrated in this invention.

BRIEF DESCRIPTION OF THE DRAWINGS

FIGS. 5-8 illustrate the opacities of copolymers of different mixtures of monomers according to this invention.

DETAILED DESCRIPTION OF THE INVENTION

Figure 1:
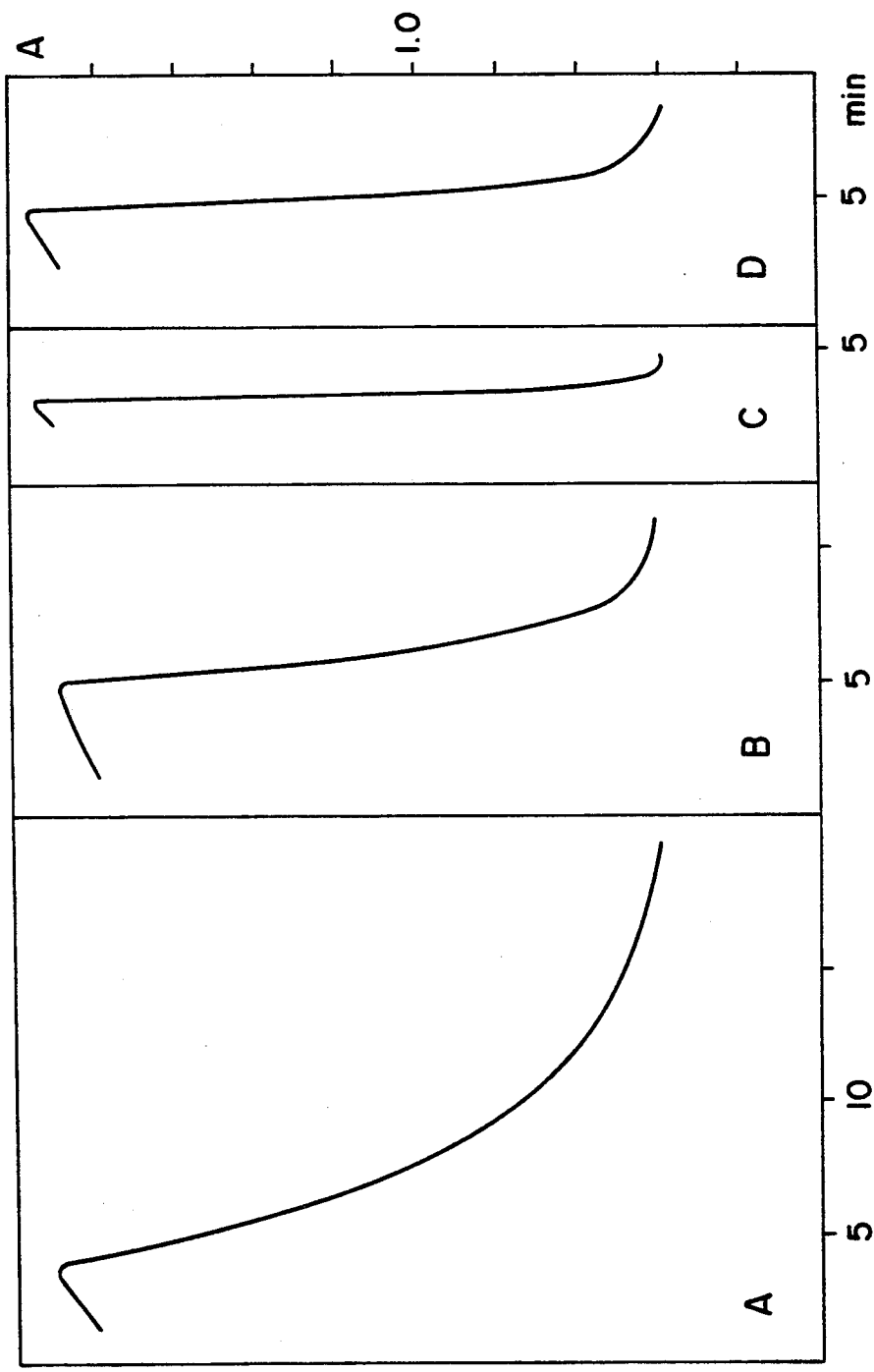
FIG. 1 is a graph comparing the polymerization rate of two monomers according to the present invention to that of acrylamide and NAT as described in Example 5.

Various aspects of the present invention are illustrated by the following examples and the accompanying drawings.

EXAMPLE 1

Synthesis of N-acryloyl-2-amino-2-deoxy-D-glucitol

The starting material for preparation of this monomer is N-acetyl-2-amino-2-deoxy-D-glucose. The synthesis includes mainly three steps, which are described below.

Step 1. N-acetyl-2-amino-2-deoxy-D-glucose was first reduced to the corresponding glucitol. Thus 0.5 mol (110.6 g) of N-acetyl-2-amino-2-deoxy-D-glucose was dissolved in about 400 ml water and the solution was cooled in an ice bath. Then 0.2 mol (7.6 g) of sodium borohydride was dissolved in about 50 ml of 1 M sodium hydroxide. This solution was added in small portions into the efficiently stirred sugar solution. The stirring process was continued for 2-4 h after all sodium borohydride had been added. At this time, there should be an excess of unreacted sodium boronhydride, which is checked by dropping one drop of the reaction solution into 50% acetic acid. If no hydrogen bubbles are generating (visible), some more NaBH$_4$ is added to the reaction mixture. (Note 1. This may be the case with too old NaBH$_4$ preparations). If hydrogen is liberated, the reaction mixture is treated with Amberlite IR-120, H$^+$. The resin was added carefully (to prevent excessive foaming) in small portions, whilst stirring and cooling in the ice bath was continued. About 200-300 ml of the resin was added. After additional stirring, there was usually very little sodium left, as detected by burning a drop of solution on platinum wire. The remaining sodium was remove by passing the reaction mixture through a 100 ml column filled with Dowex 50, H$^+$(200-400 or 100-200 mesh). The reaction mixture, which contains now N-acetyl-2-amino-2-deoxy-D-glucitol and boric acid, was evaporated under reduced pressure at 30°-40° C. The resulting syrup was mixed with about 200 ml of methanol-acetic acid solution (20:1, v/v) and evaporated. This procedure was repeated 4-5 times, and served to remove boric acid as trimethyl borate.

Step 2. The syrupy residue was dissolved in 500 ml of 2 m HCl and the solution was refluxed for 4-8 h. The solution was concentrated by evaporation and then dried in a desiccator over phosphorous pentoxide and potassium hydroxide pellets. The product, 2-amino-2-deoxy-D-glucitol hydrochloride, can be obtained in the crystalline state but this is not necessary for the next step. The yield of the crude, yellow to brownish product ranged from 3 to- 89% from four different preparations.

3. The crude 2-amino-2-deoxy-D-glucitol hydrochloride was dissolved in about 300 ml of water and the pH of this solution was adjusted to 8.0-8.5 with 5 M KOH. Then 1-2 g of sodium nitrite and 100-150 mol of methylene chloride were added, and the solution was cooled in an ice bath. Acryloyl chloride (10% molar excess over 2-amino-2-deoxy-D-glucitol) was mixed with the same volume of methylene chloride. Potassium hydroxide, equal to twice the molar amount of acryloyl chloride, was dissolved in water and cooled. The well stirred two-base reaction mixture, portions of acryloyl chloride and KOH solutions were added in such a way that the pH remained between 7.5-9.5 (as checked frequently by a narrow range pH paper). After the last additions of acryloyl chloride and KOH solutions, the reaction mixture was further stirred for about one hour (the pH was periodically checked and corrected, if necessary). The two phases were allowed to separate in a separating funnel and the lower organic phase was discarded. The aqueous phase was treated in one of two ways. A fraction of salts was precipitated with addition of four volumes of absolute ethanol and then the remaining salts were bound to the mixed ion exchangers. Alternatively, the precipitation step was omitted and the salts were directly removed by mixed ion exchangers. To the stirred solution, portions of Amberlite IR-120 H$^+$ and IRA-68 (free base) were added (pH being kept neutral or slightly acid) until the silver reaction for chloride was negative. The resin was then removed, the filtrate treated with activated charcoal and the solution poured into crystallization dishes. A small quantity (several hundred mg) of p-methoxy phenol (polymerization inhibitor) was added. The solvents evaporated within 1-2 weeks. The monomer appeared as a hard, slightly yellow but almost transparent residue. The yield ranged from 43-56% with regard to the starting materials, N-acetyl-2-amino-2-deoxy-D-glucose. The produce was pulverized and recrystallized from ethanol, m.p. 133-135 (polymerization).

Note 2. An attempt was done to prepare the same compound by reacting 2-amino-2-deoxy-D-glucose and acryloyl chloride, followed by reduction of the product with sodium boronhydride. However, it was not possible to get pure N-acryloyl-2-amino-2-deoxy-D-glucitol in this way.

EXAMPLE 2

Synthesis of N-acryloyl-N-methyl-1-amino-1-deoxy-D-glucitol

N-methyl-1-amino-1-deoxy-D-glucitol (0.5 mol, 97.6 g) was dissolved in about 300 ml of water. Then 1-2 g of sodium nitrite was added and the solution was cooled in an ice bath. Potassium hydroxide (0.6 mole) was dissolved in water and cooled. Acryloyl chloride (0.55 mole) was mixed with an equal volume of methylene chloride. The reaction was done in the same way as described in step 3 for the synthesis of N-acryloyl-2-amino-2-deoxy-D-glucitol. The salts were also removed as described above. However, even after several weeks long evaporation from a crystallization dish, the product was not dry. After addition of more polymerization inhibitor, drying was continued in a desiccator. The semi-dry mass (yield 41–60%) was dissolved in warm dioxane which contained p-methoxy phenol. The warm solution was filtered through Celite and upon cooling the crystals were formed. They were collected and recrystallized from dioxane. The title compound is very hygroscopic.

EXAMPLE 3

Synthesis of N-methacryloyl-N-methyl-1-amino-1-deoxy-D-glucitol

This compound was prepared in two slightly different ways. The first way was identical to the preparation of N-acryloyl-N-methyl-1-amino-1-deoxy-D-glucitol described above. In contrast to the previous one, this monomer readily crystallized upon drying in crystallization dishes (yield 62–80%). It was recrystallized from ethanol, m.p. 142–144.

A simpler way involved the use of lithium hydroxide instead of potassium hydroxide to neutralize hydrochloride acid that was formed during the reaction. After separation of the two phases, the water phase was without any treatment poured into crystallization dishes. After a few days in a fume cupboard, the title compound crystallized from a highly concentrated salt (mostly LiCl) solution. The crystals were collected and washed with ethanol. The yield was lower (about 50%).

EXAMPLE 4

Polymerization of N-acryloyl-2-amino-2-deoxy-D-glucitol

The monomer (450 μg) was dissolved in water to give 4.5% (w/v) solution (10 ml). To this solution were added μl of 50% (v/v) N,N,N'-tetramethylethylenediamine (TEMED) solution, followed by 155 μl of ammonium persulfate solution (15 mg/ml). The monomer solution was overlaid by diisopropyl ether. After 24 h at room temperature a highly viscous solution was produced. The polymerization of N-acryloyl-2-amino-2-deoxy-D-glucitol at high concentration (above 10%, w/v) in water usually resulted in extremely viscous polymers and/or gels that were not completely soluble in water.

EXAMPLE 5

Polymerization kinetics of N-acryloyl-2-amino-2-deoxy-D-glucitol

The polymerization kinetics (FIG. 1) of the title compound was compared to that of acrylamide (panel A) and N-acryloyltris(hydroxymethyl)aminomethane (panel B). Solutions were prepared which contained the same molar concentrations of the three monomers. The w/v concentrations were as follows: acrylamide 5%, NAT 12% and N-acryloyl-2-amino-2-deoxy-D-glucitol 16%. Polymerization of 1 ml portions was achieved by TEMED (1.5 μl) and ammonium persulfate 35 μl, 15 mg/ml). The polymerizing solution was pipetted into quartz cuvette and overlaid with diisopropyl ether. The disappearance of the double bonds was followed spectrophotometrically in the UV region. The wavelengths were chosen so that the starting absorbency was 1.8. As can be seen from FIG. 1, the title compound polymerizes much faster (panel C) than the other two monomers. Even at the lower, 10% w/v, concentration the polymerization rate (panel D) is higher than that of acrylamide and NAT.

Note 3. The higher polymerization rate indicates that the double bond of N-acryloyl-2-amino-2-deoxy-D-glucitol is more reactive than the same bond of the other two monomers and/or that there are certain interactions between a growing polymer chain and the monomer, leading to an enhancement of the polymerization rate.

EXAMPLE 6

Figure 2:
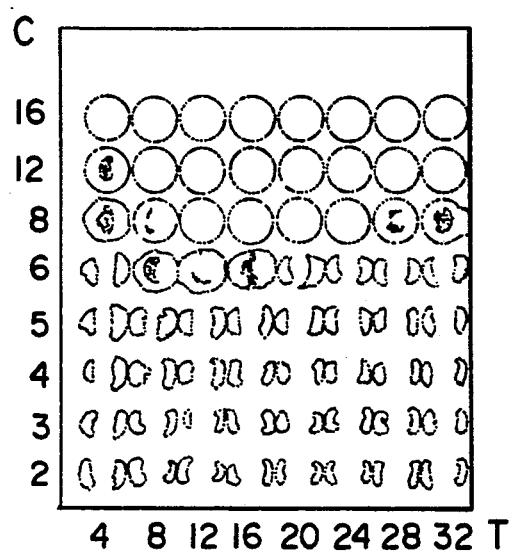
FIG. 2 is a photograph illustrating the transparency of poly-N-acryloyl-2-deoxy-D-glucitol--N,N'-methylene-bis-acrylamide gels as a function of cross-linker concentration.

Transparency of the cross-linked poly-N-acryloyl-2-amino-2-deoxy-D-glucitol-N,N'-methylene-bis-acrylamide (Bis) gels The title monomer and the cross-linker (Bis) were polymerized in 64 different combinations. The designation (T) represents total monomer concentration, which is the monomer and the cross-linker amount in grams per 100 ml of solution. The concentration of Bis (C) is expressed as weight percentage to T. From FIG. 2 one can notice the transparency of all gels containing 4 or less C. Some gels with 5 and 6 C are still transparent, whereas the gels having higher proportions of Bix became opaque. Since in most cases the transparent gels are used for electrophoresis and the opaque ones for chromatography, these results facilitate the choice of correct combinations.

EXAMPLE 7

Figure 3:
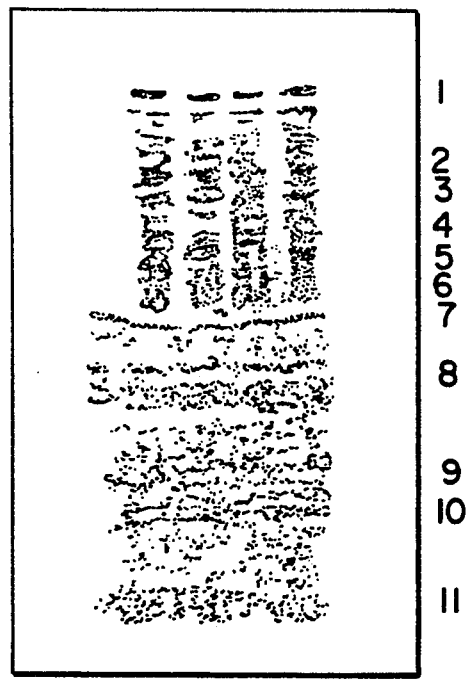
FIG. 3 is a slab gel showing the isoelectric focusing of proteins as described in Example 7.

Isoelectric focusing of proteins in a poly-N-acryloyl-2-amino-2-deoxy-D-glucitol-Bis gel The gel (T=7, C=3) was polymerized on a plastic sheet (Gel Bond), which contained polymerization double bonds. In this way the gel was covalently linked to the plastic support. After polymerization the gel was washed three times with distilled water. It was then air-dried overnight at room temperature. The broad range (3.5–10) carrier ampholytes were introduced into the gel by the overlay technique, and the pre-focusing was done for 500 Vh. The standard proteins were applied to the gel, which was run for 2600 Vh. The following standard proteins can be seen after Coomassie Brilliant Blue staining (FIG. 3): 1,trypsinogen (pI 9.3); lentil lectin basic band (pI 8.65); 3, lentil lectin middle band (pI 8.45); 4, lentil lectin acidic band (pI 8.15); 5, myoglobin basic band (pI 7.35); 6, myoglobin acidic band (pI 6.85); 7, human carbonic anhydrase (pI 6.55); 8, bovine carbonic anhydrase (pI 5.85); 9,beta-lactoglobulin A (pI 5.2); 10, soybean trypsin inhibitor (pI 4.55); 11, amyloglucosidase (pI 3 50).

EXAMPLE 8

Figure 4:
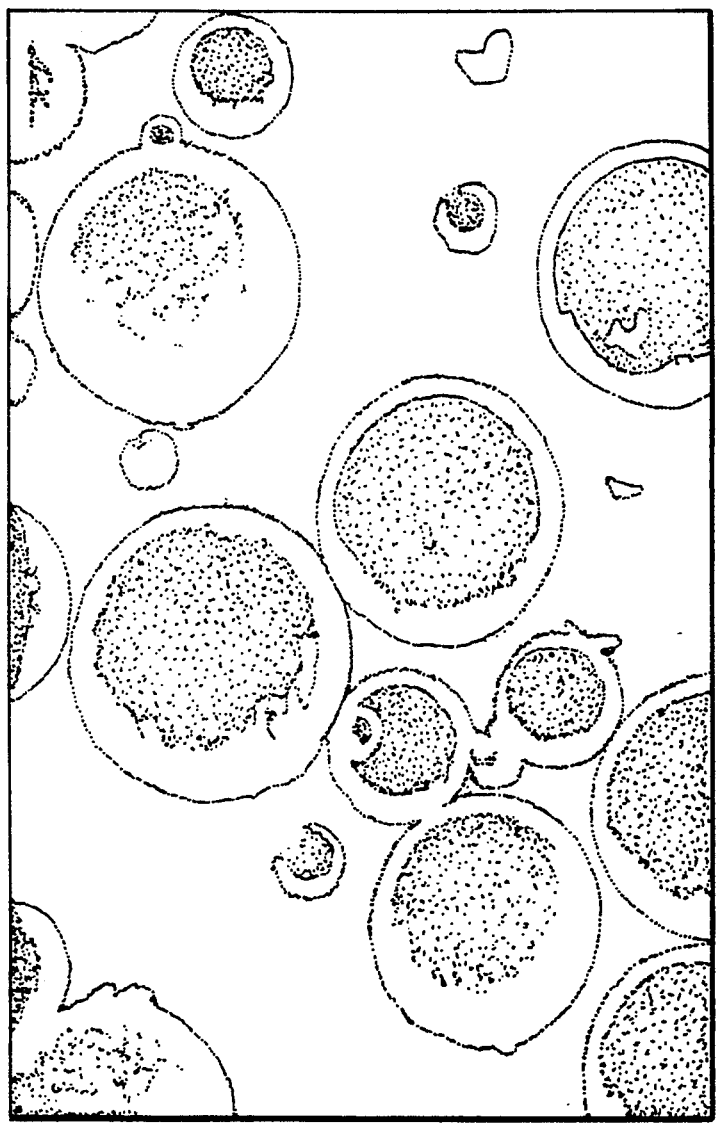
FIG. 4 is a photograph showing the opaque gel beads produced in Example 8.

Preparation of an opaque poly-N-acryloyl-2-amino-2-deoxy-D-glucitol-Bis gel in the form of beads A solution (4 ml) was prepared which contained the title monomer and the cross-linker (T=15, C=12), as well as 85 mg of poly-vinylalcohol (mW 15,000). Then, 24 ml of diethyl succinate containing 13 mg of Span 20 was deaerated (degassed), with magnetic stirring under high vacuum. This solution was then transferred into an apparatus designed for suspension polymerization (Arshady, R., and Ledwith, A. (1983) Reactive Polymers, 31 2, 2 159–174). The stirrer was inserted and a stream of nitrogen was continuously passed through the apparatus. After about 30 min, 18 μl of TEMED and 230 μl of ammonium persulfate (15 mg/ml) were added to the monomer solution, which was quickly, by means of a syringe, transferred into the apparatus. The suspension was stirred vigorously for about one hour. The formed beads were removed by gentle filtration and then washed with water by decantation. FIG. 4 shows the beads prepared in this way.

EXAMPLE 9

Synthesis of N-acryloyl-N-ethyl-1-amino-1-deoxy-D-galacitol

The N-ethyl-1-amino-1-deoxy-D-galacitol (63 g) is mixed with about 300 ml of water and 1 g of sodium nitrite. Then 100–150 ml of methylene chloride are added, and the solution is cooled in an ice bath. Acryloyl chloride (10% molar excess over the amine) is mixed with the same volume of methylene chloride. Potassium hydroxide, equal to twice the molar amount of acryloyl chloride, is dissolved in water and cooled. To the well stirred two-phase reaction mixture, portions of acryloyl chloride and KOH solutions were added in such a way that the pH remained between 7.5–9.5 (as checked frequently by a narrow range pH paper). After the last additions of acryloyl chloride and KOH solutions, the reaction mixture was further stirred for about one hour (the pH was periodically checked and corrected, if necessary). The two phases were allowed to separate in a separating funnel and the lower organic phase was discarded. The aqueous phase was treated with charcoal and filtered. The filtrate was treated with a combination of ion exchangers either in solution or by passing the filtrate through columns packed with ion exchangers. Thus, to the stirred solution, portions of Amberlite IR-120,H+ and IRA-68 (free base) were added (pH being kept neutral or slightly acid) until the silver reaction for chloride was negative. The resin was then removed, the filtrate treated with activated charcoal and the solution poured into crystallization dishes. Alternatively, the monomer solution was passed through 600 ml of IR-120 and 600 ml of IRA-68, preferentially packed in more than two columns. The solution passed always first through the cationic ion exchanger. A small quantity (several hundred mg) of p-methoxy phenol or sodium nitrite (polymerization inhibitors) were added to the monomer solution. The water evaporated within 1–2 weeks. The monomer appeared as a white solid. The yield was 72%. The monomer was recrystallized from ethanol-acetone, m.p. 80°–84° C. (polymerization).

EXAMPLE 10

Synthesis of N-acryloyl-N-propyl-1-amino-1-deoxy-D-galactitol

The synthesis was carried out substantially as described in Example 9. The yield was 75%. The monomer was recrystallized from ethanol-acetone, m.p. 128°–130° C. (polymerization).

EXAMPLE 11

Synthesis of N-acrylolyl-N-butyl-1-amino-1-deoxy-D-galactitol

The synthesis was carried out substantially as described in Example 9. The yield was 66%. The monomer was recrystallized from acetonitrile, m.p. 120°–123° C. (polymerization).

The corresponding glucitol derivative remained as a viscous aqueous solution.

EXAMPLE 12

Synthesis of N-acryloyl-N-hexyl-1-amino-1-deoxy-D-glucitol

The amine was suspended in water and mostly converted into its hydrochloride salt by addition of hydrochloric acid. The synthesis was then done essentially as described in Example 9, except that the amount of KOH needed was higher. The yield was 76%. The monomer was recrystallized from acetonitrile, m.p. 86°–88° C. (polymerization).

EXAMPLE 13

Synthesis of N-acryloyl-N-octyl-1-amino-1-deoxy-D-glucitol

The starting amine was first converted into its hydrochloride salt as described in Example 12. The synthesis was then carried out as described in Example 9. However, a larger portion of UV positive material was found in the methylene chloride than in the water phase. After evaporation of methylene chloride a slightly yellow solid mass was obtained. The crystallization attempts failed.

EXAMPLE 14

Synthesis of N-acryloyl-N-phenylethyl-1-amine-1-deoxy-D-galactitol

The starting amine was first converted mostly into its hydrochloride salt and the synthesis was then continued as described in Example 9. The yield was 37%. The monomer crystallized after evaporation of water, m.p. 52°–56° C.

EXAMPLE 15

Synthesis of N-acryloyl-N-(2-hydroxyethyl)-1-amino-1-deoxy-D-galactitol

The synthesis was done as described in Example 9. After evaporation of water the monomer appeared as a semi-solid white material. It was recrystallized from ethanol. The crystals were filtered and washed with acetone. A large portion of solvent remained within the monomer. When evaporation of the remaining solvent was tried in the air, the monomer liquified but became semi-solid again after several days. After drying in vacuo over phosphorous pentoxide, the monomer was obtained as a hard solid. It is hygroscopic.

The corresponding glucitol derivative remained as a viscous aqueous solution. When stored refrigerated as 40% solution, after several months a fungi-like semi-solid, almost transparent material appeared and grew to the size of over 3 cm.

EXAMPLE 16

Synthesis of N-acryloyl-amino-N,N,-bis(1 deoxy-D-galactitol)

The synthesis was done essentially as described in Example 9. Due to lower water solubility the amine was partially converted into its hydrochloride salt. The monomer crystallized after evaporation of water. The yield was 62%. The monomer is hardly soluble in methanol or ethanol and the crystallization attempts failed. The melting point was greatly dependent on the heating rate, being much higher (above 130° C.) at a slow rate.

The corresponding glucitol derivative remained as an aqueous solution.

EXAMPLE 17

Preparation of a water soluble polymer from N-acryloyl-N-ethyl-1-amino-1-deoxy-D-galactitol The monomer (0.3 g) and sorbitol (0.75 g) were dissolved in water and diluted to 5 ml in a glass test tube. The TEMED (12 μl) and ammonium persulfate (150 μl of a 15 mg/ml water solution) were added. The solution was overlaid with diisopropylether and polymerized overnight at room temperature. A viscous polymer solution was obtained.

EXAMPLE 18

Preparation of water soluble and insoluble copolymers from acrylamide and N-acryloyl-N-hexyl-1-amino-1-deoxy-D-glucitol Different amounts of monomers were dissolved in 50 mM Tris-HCl buffer pH 8.8 to give total monomer concentration 0.43, 0.7, 1.0, 1.29 and 1.57 M and ratios of acrylamide to the N-hexyl monomer of 7:1, 5:1 and 3:1. The solutions (300 μ) were polymerized in microtiter plates. Polymerization was started by adding to the 0.43 M solution 4 μl of TEMED and 5.9 μl of ammonium persulfate (AP, 15 mg/ml), to the 0.7 M solution 3.9 μl of TEMED and 5.7 μl of AP, to the 1 M solution 3.8 μl of TEMED and 5.5 μl of AP, to the 1.29 M solution 3.7 μl of TEMED and 5.4 μl of AP and to the 1.57 M solution 3.6 μl of TEMED and 5.3 μl of AP. Some solutions remained transparent whereas in others a precipitate was formed. In FIG. 5, soluble polymers are shown as white, not dotted, circles, precipitated polymers as dotted circles, stronger dotted for more precipitated polymers. The solubility clearly depends on the total monomer concentration as well as the molar ratio of acrylamide to the amphiphatic monomer.

A 10 ml solution of acrylamide and N-acryloyl-N-hexyl-1-amino1-deoxy-D-glucitol containing 4% (w/v) total monomer and 7:1 molar ratio of acrylamide to N-hexyl monomer was polymerized with 10 μl of TEMED and 120 μl of ammonium persulfate (15 mg/ml). There resulted a viscous solution which foamed after agitation.

EXAMPLE 19

Preparation of water soluble and insoluble copolymers from N- c acryloyl-1-amino-1-deoxy-D-glucitol and N-acryloyl-N-hexyl-1-amino1-deoxy-D-glucitol Twelve solutions were prepared by having different molar ratios and total concentrations of monomers as described in Example 18. After polymerization, the same TEMED and AP concentrations were used in Example 18, in the microtiter wells the result shown in FIG. 6 was obtained. Most combinations gave polymers which did not form visible precipitates. This is in contrast with copolymers comprising acrylamide instead of N-acryloyl-1-amino-1-deoxy-D-glucitol, demonstrating that copolymers with a higher amount of hydrophobic residues remain water soluble by increasing the hydrophilicity of the hydrophilic monomer.

A 5 ml water solution of N-acryloyl-1-amino-1-deoxy-D-glucitol andN-acryloyl-N-hexyl-1-amino-1-deoxy-D-glucitolcontaining0.75 g sorbitol and 6% (w/v) total monomer wit 10:1 molar ratio of the hydrophilic to amphiphatic monomer was polymerized by addition of 8 μl TEMED and 100 μl ammonium persulfate (15 mg/ml). There resulted a viscous solution foamed upon agitation.

When the total monomer concentration was increased to 9% (w/v) or above, it was not possible to obtain polymers which completely dissolved after dilution with water.

EXAMPLE 20

Transparent and opaque gels from acrylamide, N-acryloyl-N-hexyl-1-amino-1-deoxy-D-glucitol and N,N'-methylene-bis-acrylamide Fifteen solutions were polymers which contained form 0.43 to 1.57 M total monomer concentration and molar ratios of acrylamide to the N-hexyl monomer from 3:1 to 7:1. The same amount of TEMED and AP as described in Example 18 were added. Each solution contained the same percentage of the cross-linker (C=1%, w/w) in relation to the total monomer. In FIG. 7 the transparent gels are represented by white circles without dots and opaque gels by circles with dots. The opacity of gels is dependent on the total monomer concentration as well as the ration of acrylamide and the amphiphatic monomer.

EXAMPLE 21

Transparent and opaque gels from N-acryloyl-I-amino-1-deoxy-D-glucitol, N-acryloyl-N-hexyl-1-amino-1-deoxy-D-glucitol and N,N'-methylene-bis-acrylamide Twelve solutions were polymerized which contained from 0.43 to 1.29 M total monomer and from 3:1 to 7:1 molar ratio of the hydrophilic to the amphiphatic monomer. Each solution had the same percentage of the cross-linker (C=1%, w/w) in relation to the total monomer. FIG. 8 shows that most combinations yielded transparent gels. That is different to the result obtained with acrylamide (Example 20), where most combinations yielded slightly to fully opaque gels.

EXAMPLE 22

A transparent gel from N-acryloyl-N-butyl-1-amino-1-deoxy-Dgalacitol and 1,2-dihydroxyethylene-bis-acrylamide To a 5 ml water solution of the monomers (T=8%, C=3%) in a glass test tube TEMED (9 μl) and ammonium persulfate (100 μl, 15 mg/ml solution) were added. After two hours a transparent gel was formed.

EXAMPLE 23

Electrophoresis in the gel prepared from N-acryloyl-N-(2-hydroxyethyl)-1-amino-1-deoxy-D-glucitol and N,N'-methylene-bis-acrylamide.

As described in example 15, this monomer was obtained as a concentrated water solution. That solution was treated with a mixture of ion exchangers (containing a blue indicator, from Bio Rad) and then with activated charcoal. The solution was first filtered through a filter paper and then through a nitrocellulose membrane filter (0.45 μm). The concentration of the monomer solution was estimated by measuring the absorbance at 260 nm of the appropriately diluted sample and comparing it to the standard curve obtained with crystaline N-acryloyl-N-methyl-1-amino-1-deoxy-D-galactitol.

The concentrated solution was 40% (w/v). A part of it was diluted to give a 7% solution in 30 mM Tris-acetate buffer pH 8.4, containing 2 mM ethylenediaminetetra-acetic acid. In 20 ml of this solution N,N'-methylene-bis-acrylamide (42 mg) was dissolved to give C=3%. Then TEMED (23 μl) and ammonium persulfate (270 μl 15 mg/ml) were added and the gel polymerized in a plastic cassette (7×10 cm), having sample well formers about 5 mm apart from edge of the shorter side. lhe gel was approximately 3 mm thick and the sample wells were about 3 mm deep and 5 mm long. The gel was polymerized on a plastic support (PAGE GelBond, FMC). After 4 hours at room temperature, the cassette was opened and the gel placed in an electrophoretic apparatus for submerged gel electrophoresis. The apparatus (home made) was equipped with a pump for buffer circulation and the gel rested on a cooling plate. Three different DNA standard mixtures were applied to the gel. They included 1 kbp ladder (from BRL), 123 bp ladder (from BRL and lambda/Hind III fragments (from Biofinex). The gel was run at 20° C. in 30 mM Tris-acetate buffer pH 8.4, containing 2 mM EDTA at 4 V/cm for 4 hours. Then it was stained with ethidium bromide (1 μg/ml) and distained with water. DNA bands were visualized under UV light. All DNA fragments migrated further than in the poly(NAT-Bis) gel (T=7%, C=3) which was run as a control, demonstrating a larger effective pore size. In the 1 kbp ladder, 506 and 516 DNA bands were clearly resolved as were 3 and 4 kbp bands. In the 123 bp ladder, at least 12 bands well resolved. In the lambda/Hind III mixture, the 2.0 and 2.2 kbp fragments were well resolved.

EXAMPLE 24

Electrophoresis in the gel prepared from N-acryloyl-amino-N,Nbis(1-deoxy-D-galacitol) and N,N'-methylene-bis-acrylamide The monomer (1 6 g) and the cross-linker (48 mg) were dissolved in 10 ml of water and the solution treated with mixed ion exchanger and charcoal as described in Example 23. The filtered solution was diluted to 20 ml with 60 mM Tris-acetate pH 8.,4, containing 4 mM EDTA. The gel was then polymerized, run and stained as described in Example 23. All DNA fragments migrated much further than in the corresponding poly(-NAT-Bis) gel and somewhat further than the gel of Example 23. The bands were slightly broader than in the gel of Example 23. In the 1 kbp ladder 506 and 516 DNA bands were resolved and in 123 bp ladder at least 10 bands were clearly visible.

EXAMPLE 25

Electrophoresis in the gel prepared from N-acryloyl-N-ethyl-1-amino-1-deoxy-D-galacitol and N,N'-methylene-bis-acrylamide.

The gel (T=6%, C=3%) solution was prepared by dissolving the monomer and cross-linker in the running buffer. The solution was polymerized to a perfectly transparent gel, which was run for 3 h at 4 V/cm and stained as described in Example 23. The bromphenol blue migrated slightly ahead of 123 bp fragment. In the 1 kbp ladder, 506 and 516 bp bands were resolved and the distances between upper bands were slightly larger than in the corresponding N-acryloyl-N-methyl-1-amino-1-deoxy-D-galacitol gel run as a control at the same time. In the 123 bp ladder, at least 13 bands were distinguishable. In the lambda/Hind III fragments, 2.0 and 2.2 kbp bands were resolved. After electrophoresis the gel was somewhat swollen (thicker) and swelling becomes more pronounced during staining and destaining. Such swelling was not noticed with other gels examined. Once the gel detached from the supporting plastic.

EXAMPLE 26

Electrophoresis in the gel prepared from N-acryloyl-N-propyl-1-amino-1-deoxy-D-galacitol and N,N'-methylene-bis-acrylamide.

The gel was prepared and run essentially as described in Example 25. The gel was very slightly opaque, which was noticeable when looking through the long side of the gel. The DNA bands were somewhat sharper and better resolved than in the gel of Example 25, although the migration distances were comparable. Bromphenol blue migrated in this gel approximately as the 246 bp fragment. The 506 and 516 bp bands were well resolved and at least 13 bands were distinguishable in the 123 bp ladder. The 2.0 and 2.2 kbp bands were also well resolved.

EXAMPLE 27

Electrophoresis in the gel prepared from N-acryloyl-N-butyl-1-amino-1-deoxy-D-galacitol and N,N'-methylene-bis-acrylamide.

The gel was prepared and run essentially as described in Example 25. This gel was considerably more opaque than the gel of Example 26. The DNA fragments migrated a similar distance but the bands were generally broader. The 506 and 516 bp were distinguishable and the 2.0 and 2.2 kbp were resolved, although not so well as in other gels. Bromphenol blue concentrated as it entered the gel and it also changed the color (to paler blue). At the end of the run bromphenol blue migrated approximately the same distance as the 1 kbp band from the 1 kbp ladder. This gel was mechanically weaker than the previous two gels and had a tendency to detach from the plastic support.

EXAMPLE 28

Figure 9:
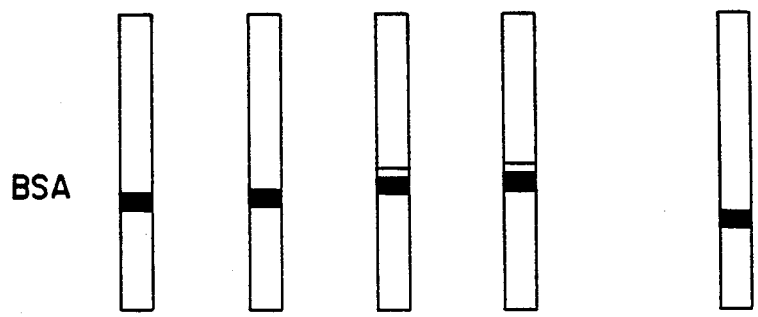
FIGS. 9-12 illustrate the separations achievable in porous gels according to this invention for copolymers of differing ratios of different monomers.

Electrophoresis in the gels prepared from N-acryloyl-N-hexyl-1-amino-1-deoxy-D-glucitol, acrylamide and N,N'-methylene-bis-acrylamide in the presence of 0.02% SDS The gels (T=12%, C=1%) contained various molar ratios of acrylamide and the N-hexyl monomer. The gel was polymerized in 0.375 M Tris-HCl pH 8.8 containing 0.02% SDS in glass tubes (inner diameter 4 mm, lengthy 7 cm). A stacking gel (T=4%, C=1%) was polymerized in 0.125 M Tris-HCL pH 6.8. The running buffer was 50 mM Tris-0.384 M glycine buffer pH 8.3. Bovine serum albumin heated in the stacking gel buffer containing 1% SDS and 3% mercaptoethanol and applied to the gel. The gels were run until bromphenol blue in the control gel reached the bottom of the gel. Proteins were detected by Coomassie Brilliant Blue R-250 staining. As shown in FIG. 9, the migration of BSA was dependent on the ratio of acrylamide and the N-hexyl monomer, slightly decreasing in the gels with higher amounts of the amphiphatic monomer. The first gel was polymerized without N-acryloyl-N-hexyl-1-amino-1-deoxy-D-glucitol (1-NHAGU), the last one with N-acryloyl-1-amino-1-deoxy-D-glucitol (1-NAGA, 20 : 1 molar ratio).

EXAMPLE 29

Figure 10:
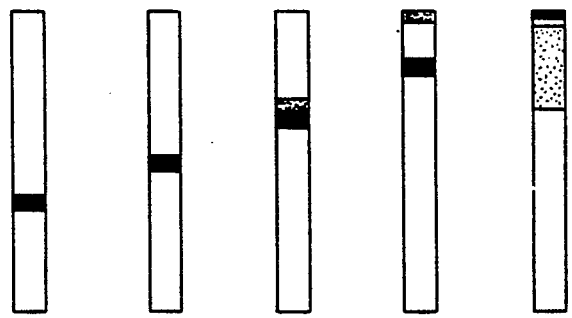

Electrophoresis in the gels prepared from N-acryloyl-N-hexyl-1-amino-1-deoxy-D-glucitol, acrylamide and N,N'-methylene-bis-acrylamide in the presence of 0.05% SDS The gels were prepared and run as described in Example 28. At this higher concentration of SDS the protein was retarded even in the gel with 160:1 molar ratio of acrylamide to the N-hexyl monomer, as shown in FIG. 10. BSA migrated only very little in the gel with the 20:1 ratio.

EXAMPLE 30

Figure 11:
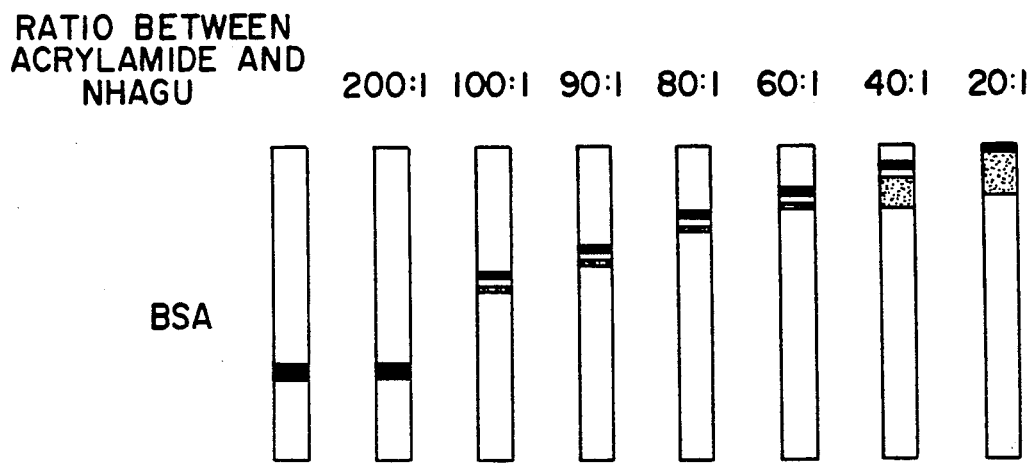

Electrophoresis in the gels prepared from N-acryloyl-N-hexyl-1-amino-1-deoxy-D-glucitol, acrylamide and N,N'-methylene-bisacryla in the presence of 0.1% SDS The gels were prepared and run as described in Example 28. As can be seen from FIG. 11, in the 90:1 gel BSA migrated approximately half the distance it migrated in the gel without 1NHAGU (first gel) and it hardly entered the 20:1 gel.

EXAMPLE 31

Figure 12:
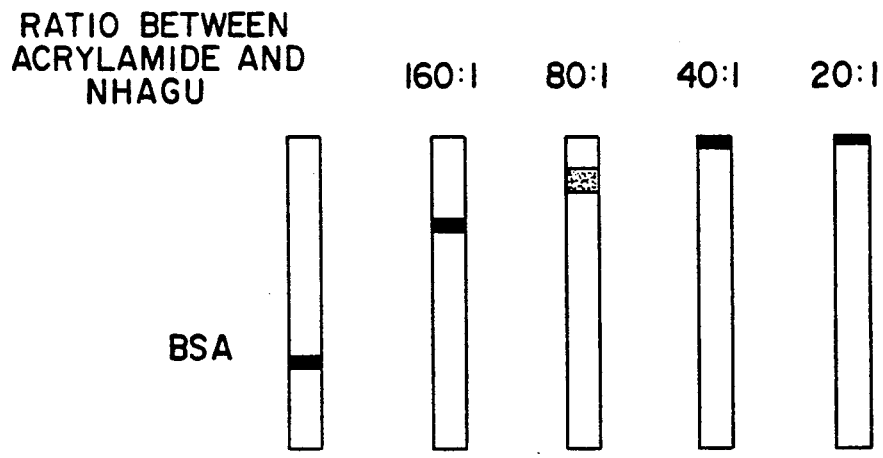

Electrophoresis in the gels prepared from N-acryloyl-N-hexyl-1-amino-1-deoxy-D-glucitol, acrylamide and N,N'-methylene-bisac in the presence of 0.2% SDS The gels were prepared and run as described in Example 28. FIG. 12 shows that in the 160:1 gel BSA migrated less than half the distance it migrated in the gel without 1-NHAGU (first gel). The protein remained on the top of 40:1 and 20:1 gels.

As is clear from the preceding examples, the gel of the present invention is useful as a separation medium in isoelectric focusing, electrophoresis and chromatography for resolving proteins according to their size or charge or their hydrophobicity or their affinity for a molecule that is bound to the gel, to resolve nucleic acids or polynucleotides, to determine the sequence of nucleic acids and to resolve other charged molecules.

REFERENCES

1. Kozulic, M., Kozulic, B., and Mosbach K. (1987) Anal. Biochem. 163, 506–512
2. Kozulic, B., Mosbach, K, and Pietrzak, M. (1988) Anal. Biochem. 170, 478–484
3. Kozulic, B., and Mosbach K. (1988) Patent Application, PCT/EP88/00515
4. Park, T.G., and Hoffman, A.S. (1990) Journal of Biomedical Materials Research 24, 21–38
5. von Morze, Herwig, European Patent Application 83303047.1
6. European Patent Application 79102502.6
7. European Patent Application 80103828.6
8. Hodge, J.E., and Moy, B.F. (1963) J. Org. Chem. 28,2784–2789
9. Morgan, S.E., and McCormick, C.L. (1990) Prog. Polym. Sci. 15,
10. Goubran R., and Garti, N. (1988) J. Dispersion Science And Technology 9, 131–148
11. Laemmli, U.K. (1970) Nature 277, 680–685
12. Terabe, S., Otsuka, K., Ichikawa, K., Tsuchiya, A., and Ando, T. (1984) Anal. Biochem. 56, 111–113

We claim:

1. An acrylic monomer of sufficient purity to form reproducible gels suitable for use in electorphoresis of the formula

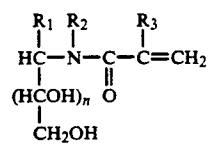

where
$R_1$ is H or $(CHOH)_m CH_2OH$, m being 0,1 or 2;
$R_2$ is monohydroxyalkyl, polyhydroxyalkyl or hydrocarbon radical;
$R_3$ is H or $CH_3$; and
n is an integer of 1–4.

2. The monomer of claim 1 wherein $R_2$ is hydrocarbon of 1 to 30 carbon atoms.

3. The monomer of claim 1, n-acryloyl-N-ethyl-1-amino-1-deoxy -D-galactitol.

4. The monomer of claim 1, N-acryloyl-N-propyl-1-amino-1-deoxy -D-galactitol.

5. The monomer of claim 1, N-acryloyl-N-butyl-1-amino-1-deoxy -D-galactitol.

6. The monomer of claim 1, N-acryloyl-N-hexyl-1-amino-1-deoxy-D-glucitol.

7. The monomer of claim 1, N-acryloyl-N-octyl-1-amino-1- deoxy-D-glucitol.

8. The monomer of claim 1, N-acryloyl-N-phenylethyl-l-amino 1-deoxy-D-galactitol.

9. The monomer of claim 1, N-acryloyl-N-(2-hydroxyethyl)-1- amino-1-deoxy-D-glucitol.

10. The monomer of claim 1, N-acryloyl-N-(2-hydroxyethyl)-1- amino-1-deoxy-D-galactitol.

11. The monomer of claim 1, N-acryloyl-amino-N,N-bis(1-deoxy- D-galactitol).

12. The monomer of claim 1, N-acryloyl-amino-N,N-bis(1-deoxy- D-glucitol).

13. The monomer of claim 1, N-acryloyl-N-methyl-1-amino-1- deoxy-D-glucitol.

14. The monomer of claim 1, N-methacryloyl-N-methyl-1-amino- -deoxy-D-glucitol.

15. The monomer of claim 1, N-acryloyl-N-methyl-1-amino-deoxy -D-xylitol.

16. The monomer of claim 1, N-methacryloyl-N-methyl-1-amino-1-deoxy -D-xylitol.

17. A process for preparing an acrylic monomer of the formula:

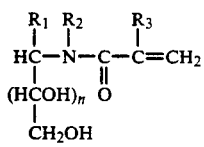

where

R₁ H, CH₂OH or (CHOH)ₘCH₂OH, m being 1 or 2;

R₂ is [H or ] CH₃;

R₃ is H or CH₃; and n is an integer of 1-4;

comprising reacting the amino group of an aminodeoxy-sugar alcohol with an acryloyl or methacryloyl chloride; and subjecting the reaction products to ion exchange treatment sufficient to remove substantially all of the charged polymerizable compounds therefrom.

18. A process or preparing amino sugar acrylamides of the formula:

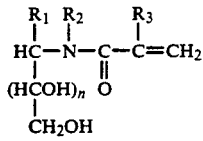

where
R₁ is H, CH₂OH or (CHOH)ₘCH₂OH, m being 1 or 2;
R₂ is hydrogen, monohydroxyalkyl, polyhydroxyalkyl or hydrocarbon radical;
R₃ is H or CH₃; and n is an integer of 1-4;
which comprises:
dissolving an acryloyl halide in a halogenated hydrocarbon solvent therefor; adding said solution to a water solution of an amino sugar alcohol to form a two-phase system; adjusting the pH of said system to about 7 to 9; subjecting said system to conditions sufficient to support the reaction of said acryloyl halide and said amine sugar alcohol; treating the reaction product water phase to both anion and cation exchange sufficient to remove substantially all charged compounds therefrom and leaving said monomer in a water solution; and drying said water solution to thereby recover said monomer.

19. The process as claimed in claim 18 wherein said acryloyl halide is acryloyl chloride.

20. The process as claimed in claim 3 wherein said acryloyl halide is methacryloyl chloride.

* * * * *